United States Patent [19]

James et al.

[11] Patent Number: 4,652,674

[45] Date of Patent: Mar. 24, 1987

[54] METHOD FOR MONITORING THE FLUORESCENCE OF 4-CARBOXY-P-TERPHENYL IN CRUDE TEREPHTHALIC ACID

[75] Inventors: David E. James, Batavia; Neal R. Nowicki; Robert W. McCoy, both of Naperville, all of Ill.

[73] Assignee: Amoco Corporation, Chicago, Ill.

[21] Appl. No.: 800,726

[22] Filed: Nov. 22, 1985

[51] Int. Cl.$^4$ ................... G01N 21/64; G01N 30/02; C07C 51/42

[52] U.S. Cl. ................... 562/414; 436/129; 436/161; 436/172; 562/487

[58] Field of Search ............... 562/414, 487; 436/129, 436/172, 161; 210/656

[56] References Cited

U.S. PATENT DOCUMENTS

| | | | |
|---|---|---|---|
| 3,584,039 | 6/1971 | Meyer | 562/487 X |
| 3,726,915 | 4/1973 | Pohlmann | 562/487 |
| 4,405,809 | 9/1983 | Stech et al. | 562/487 |

Primary Examiner—Arnold Turk
Attorney, Agent, or Firm—James R. Henes; William H. Magidson; Ralph C. Medhurst

[57] ABSTRACT

A method is disclosed for separating and measuring the fluorescence of 4-carboxy-p-terphenyl in crude terephthalic acid formed by the liquid-phase oxidation of p-xylene in a solvent.

9 Claims, 1 Drawing Figure

METHOD FOR MONITORING THE FLUORESCENCE OF 4-CARBOXY-P-TERPHENYL IN CRUDE TEREPHTHALIC ACID

BACKGROUND OF THE INVENTION

1. Field of the Invention

This invention relates generally to a method for monitoring the fluorescence of 4-carboxy-p-terphenyl in crude terephthalic acid formed by the liquid-phase oxidation of p-xylene in a solvent, and more particularly concerns the measurement of the fluorescence of 4-carboxy-p-terphenyl separated from the crude terephthalic acid by isocratic, high performance liquid chromatography.

2. Discussion of the Prior Art

Polymer grade or "purified" terephthalic acid is the starting material for polyethylene terephthalate, which is the principal polymer for polyester fibers, polyester films, and resins for bottles and like containers. Purified terephthalic acid is derived from relatively less pure, technical grade or "crude" terephthalic acid by purification of the latter utilizing hydrogen and a noble metal catalyst as described in U.S. Pat. No. 3,584,039 to Meyer. In the purification process, the impure terephthalic acid is dissolved in water at an elevated temperature, and the resulting solution is hydrogenated, preferably in the presence of a hydrogenation catalyst, e.g., palladium on a carbon support, as described in U.S. Pat. No. 3,726,915 to Pohlmann. This hydrogenation step converts the various color bodies present in the relatively impure terephthalic acid to colorless products. Another related purification-by-hydrogenation process for aromatic polycarboxylic acids produced by liquid phase catalyst oxidation of polyalkyl aromatic hydrocarbons is described in U.S. Pat. No. 4,405,809 to Stech et al.

Even after the purification of crude terephthalic acid produced by the liquid-phase oxidation of p-xylene in a solvent by the aforesaid well-known procedures, the resulting purified terephthalic acid contains impurities which fluoresce at wavelengths of greater than 370 nanometers, preferably 390–400, nanometers produced by excitation wavelengths of 260–320 nanometers. Since the concentration of such impurities in the purified terephthalic acid can vary significantly, specifications are often established for the amount of such fluorescence which can be permitted for the purified terephthalic acid product.

Known methods for measuring the aforesaid fluorescence of purified terephthalic acid are available. However, several hours are required to purify the crude terephthalic acid and obtain a sample of the resulting purified terephthalic acid that is suitable for use in fluorescence measurements. Thus, while such purification operation is being performed and samples of purified terephthalic acid are being obtained, substantial quantities of a purified terephthalic acid product which is unacceptable to customers may be made. The method of the present invention permits this problem to be avoided by measuring the fluorescence of 4-carboxy-p-terphenyl, at wavelengths of greater than 370 nanometers produced by excitation wavelengths of 260–320 nanometers, in the crude terephthalic acid before it is purified and thereby estimating and monitoring the fluorescence, at wavelengths of greater than 370 nanometers produced by excitation wavelengths of 260–320 nanometers, of the purified terephthalic acid to be produced from it.

OBJECTS OF THE INVENTION

It is therefore a general object of the present invention to provide an improved method which overcomes the aforesaid problem of prior art methods, for monitoring the fluorescence of purified terephthalic acid obtained from crude terephthalic acid produced by the liquid-phase oxidation of p-xylene with an oxygen-containing gas in a solvent and in the presence of an oxidation catalyst.

More particularly, it is an object of the present invention to provide an improved method for monitoring the fluorescence of purified terephthalic acid obtained from crude terephthalic acid produced by the aforesaid liquid-phase oxidation of p-xylene by measuring the fluorescence of a single impurity in crude terephthalic acid.

Other objects and advantages of the invention will become apparent upon reading the following detailed description and appended claims, and upon reference to the accompanying drawings.

SUMMARY OF THE INVENTION

These objects are achieved by the method of this invention for use in combination with a method for producing purified terephthalic acid comprising: oxidizing in the liquid-phase p-xylene with an oxygen-containing gas in a solvent at an elevated temperature and pressure and in the presence of an oxidation catalyst comprising cobalt, manganese, and bromine components to form crude terephthalic acid and impurities comprising 4-carboxy-p-terphenyl; reducing in the liquid phase at least a portion of the impurities in the resulting crude terephthalic acid in an aqueous solution at an elevated temperature and pressure and in the presence of hydrogen and at least one insoluble Group VIII noble metal-containing catalyst; separating the solid noble metal-containing catalyst from the aqueous solution; and crystallizing and separating the purified terephthalic acid from the aqueous solution while maintaining the temperature in the range of 50°–150° C. The method of this invention for monitoring the fluorescence at wavelengths of greater than 370 nanometers produced by excitation wavelengths of 260–320 nanometers of 4-carboxy-p-terphenyl in the crude terephthalic acid, and variations therein, comprises separating 4-carboxy-p-terphenyl from a sample of the crude terephthalic acid having a predetermined optical density at a wavelength of 340 nanometers by isocratic, high performance liquid chromatography, using a reversed-phase nonpolar stationary phase and a mobile phase comprising: (1) from about 0.5 to about 10 volume percent of at least one of acetic acid, formic acid or an inorganic buffer, (2) from about 20 to about 90 volume percent of at least one of acetonitrite, tetrahydrofuran, methanol, ethanol, or isopropanol, and (3) from about 20 to about 80 volume percent of water and has a pH of from about 2 to about 5; and measuring the fluorescence of the separated 4-carboxy-p-terphenyl at wavelengths of greater than 370 nanometers produced by excitation wavelengths of 260–320 nanometers, to thereby monitor the fluorescence, and variations therein, of purified therephthalic acid at wavelengths of greater than 370 nanometers produced by excitation wavelengths of 260–320 nanometers.

BRIEF DESCRIPTION OF THE DRAWING

For a more complete understanding of this invention, reference should now be made to the embodiments illustrated in greater detail in the accompanying drawing and described below by way of examples of the invention. In the drawing.

DETAILED DESCRIPTION OF THE PREFERRED EMBODIMENTS

Figure 1:
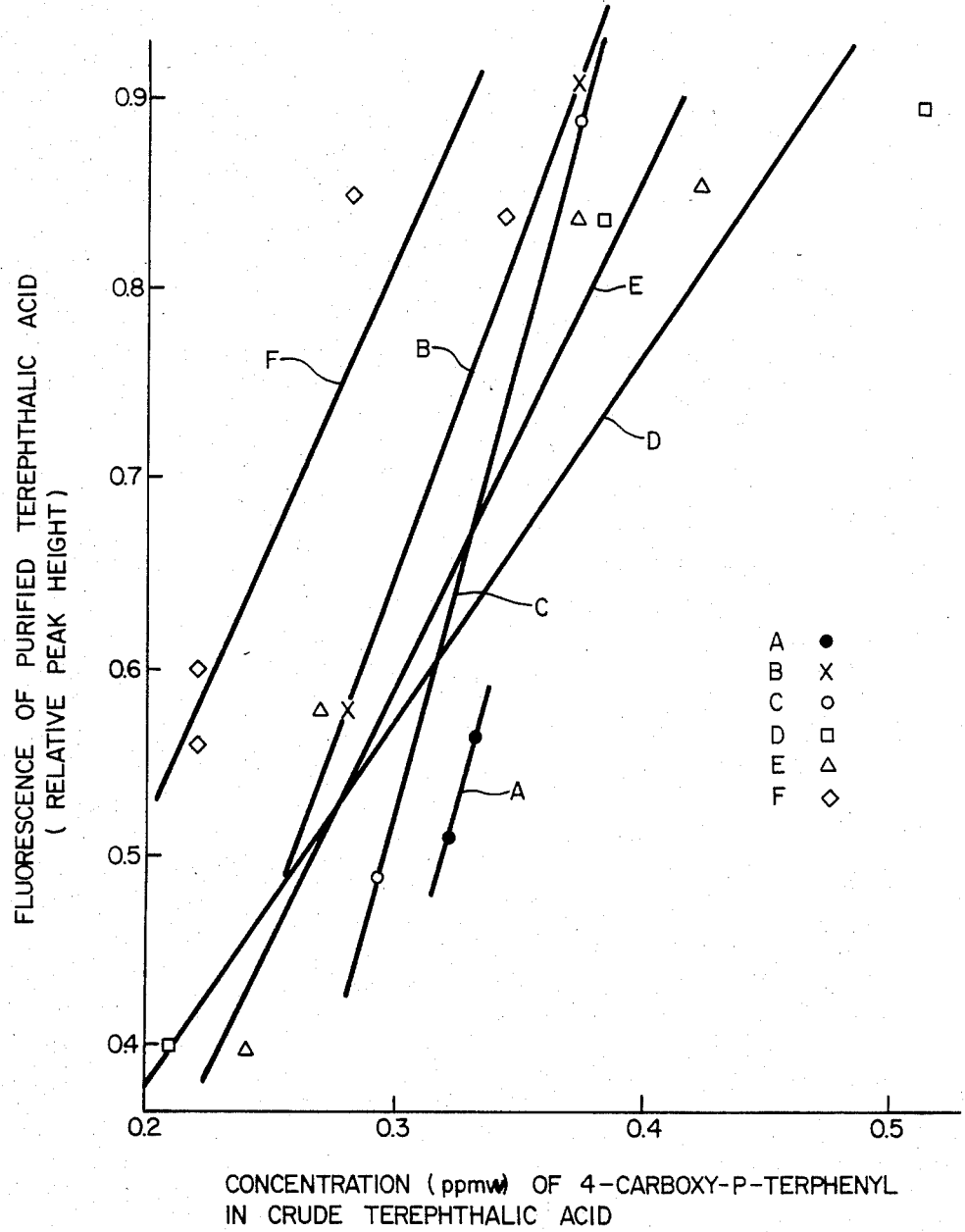
FIG. 1 is a series of plots of the fluorescence of purified terephthalic acid products at wavelengths of 390–400 nanometers produced by excitation wavelengths of 260–320 nanometers versus the concentration of 4-carboxy-p-terphenyl in the crude terephthalic acid products from which such purified products were obtained.

Suitable solvents for use in the oxidation step of the method for producing purified terephthalic acid for use in combination with the method of this invention include any aliphatic $C_2$–$C_6$ monocarboxylic acid such as acetic acid, propionic acid, n-butyric acid, isobutyric acid, n-valeric acid, trimethylacetic acid, and caproic acid and water and mixtures thereof. Preferably, the solvent is a mixture of acetic acid and water, which more preferably contains from 1 to 20 weight percent of water, as introduced into the oxidation reactor. Since heat generated in the highly exothermic liquid-phase oxidation is dissipated at least partially by vaporization of solvent in the oxidation reactor, some of the solvent is withdrawn from the reactor as a vapor, which is then condensed and recycled to the reactor. In addition, some solvent is withdrawn from the reactor as a liquid in the product stream. After separation of the crude terephthalic acid product from the product stream, at least a portion of the mother liquor (solvent) in the resulting product stream is generally recycled to the reactor.

The source of molecular oxygen employed in the oxidation step of the method for producing purified terephthalic acid for use in combination with the method of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture containing from 0.5 to 8 volume percent oxygen (measured on a solvent-free basis). For example, a feed rate of the oxygen-containing gas sufficient to provide oxygen in the amount of from 1.5 to 2.8 moles per methyl group will provide such 0.5 to 8 volume percent of oxygen (measured on a solvent-free basis) in the gas-vapor mixture in the condenser.

The catalyst employed in the oxidation step of the method for producing purified terephthalic acid for use in combination with the method of this invention comprises cobalt, manganese, and bromine components, and can additionally comprise accelerators known in the art. The weight ratio of cobalt (calculated as elemental cobalt) in the cobalt component of the catalyst-to-polyalkyl aromatic in the liquid-phase oxidation is in the range of from about 0.2 to about 10 milligram atoms (mga) per gram mole of polyalkyl aromatic. The weight ratio of manganese (calculated as elemental manganese) in the manganese component of the catalyst-to-cobalt (calculated as elemental cobalt) in the cobalt component of the catalyst in the liquid-phase oxidation is in the range of from about 0.2 to about 10 mga per mga of cobalt. The weight ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is in the range of from about 0.2 to about 1.5 mga per mga of total cobalt and manganese.

Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromine can be employed. The 0.2:1.0 to 1.5:1.0 bromine-to-total cobalt and manganese milligram atom ratio is provided by a suitable source of bromine. Such bromine sources include elemental bromine ($Br_2$), or ionic bromide (for example, HBr, NaBr, KBr, $NH_4Br$, etc.), or organic bromides which are known to provide bromide ions at the operating temperature of the oxidation (e.g., bromobenzenes, benzylbromide, mono- and di-bromoacetic acid, bromoacetyl bromide, tetrabromoethane, ethylene-di-bromide, etc.). The total bromine in molecular bromine and ionic bromide is used to determine satisfaction of the elemental bromine-to-total cobalt and manganese milligram atom ratio of 0.2:1.0 to 1.5:1.0. The bromine ion released from the organic bromides at the oxidation operating conditions can be readily determined by known analytical means. Tetrabromoethane, for example, at operating temperatures of 170° to 225° C. has been found to yield about 3 effective gram atoms of bromine per gram mole.

In operation, the minimum pressure at which the oxidation reactor is maintained is that pressure which will maintain a substantial liquid phase of the polyalkyl aromatic and at least 70 percent of the solvent. The polyalkyl aromatic and solvent not in the liquid phase because of vaporization is removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 kg/cm$^2$ to about 35 kg/cm$^2$, and typically are in the range of from about 10 kg/cm$^2$ to about 30 kg/cm$^2$. The temperature range within the oxidation reactor is generally from about 120° C., preferably from about 150° C., to about 240° C., preferably to about 230° C. The solvent residence time in the oxidation reactor is generally from about 20 to about 150 minutes and preferably from about 30 to about 120 minutes.

Crude terephthalic acid produced by the liquid-phase oxidation of p-xylene is generally purified by reduction of the impurities therein, for example, by the methods disclosed in the aforesaid U.S. Pat. Nos. 3,584,039; 3,726,915; and 4,405,809. The purification step of the method for producing purified terephthalic acid for use in combination with the method of the present invention is conducted at an elevated temperature and pressure in a fixed catalyst bed. The crude terephthalic acid to be purified is dissolved in water or a like polar solvent. Although water is the preferred solvent, other suitable polar solvents include the relatively lower molecular weight alkyl carboxylic acids, alone or admixed with water. Suitable reactor temperatures for use in this purification step are in the range of from about 100° C. to about 350° C. Preferably, the temperatures employed in the purification step are in the range of about 275° C. to about 300° C.

The pressure employed in the purification step depends primarily upon the temperature employed therein. Inasmuch as the temperatures at which practical amounts of the impure terephthalic acid may be dissolved in an aforesaid solvent are substantially above the normal boiling point of the solvent, the process pressures are necessarily considerably above atmospheric pressure to maintain the aqueous solution in liquid phase. If the reactor is hydraulically full, the reactor pressure can be controlled by the feed pumping rate. If the reactor has a head space, the reactor pressure can be maintained by gaseous hydrogen alone or in admixture with an inert gas such as water vapor and/or nitrogen in the head space. The use of an inert gas in admixture with hydrogen also can provide an advantageous means for modulating the reactor hydrogen partial pressure, especially at relatively low hydrogen partial pressures. To this end, the inert gas preferably is admixed with hydrogen prior to introduction into the reactor. In general, the reactor pressure during hydrogenation can be in the range of about 200 to about 1,500 pounds per square inch gauge (psig), and usually is in the range of about 900 psig to about 1,200 psig.

The reactor employed in the purification step can be operated in several modes. For example, a predetermined liquid level can be maintained in the reactor, and hydrogen can be fed in, for any given reactor pressure, at a rate sufficient to maintain the predetermined liquid level. The difference between the actual reactor pressure and the vapor pressure of the terephthalic acid solution present is the hydrogen partial pressure in the reactor vapor space. Alternatively, if hydrogen is fed in admixture with an inert gas such as nitrogen, the difference between the actual reactor pressure and the vapor pressure of the terephthalic acid solution present is the combined partial pressure of hydrogen and the inert gas admixed therewith. In this case the hydrogen partial pressure can be calculated from the known relative amounts of hydrogen and inert gas present in the admixture.

In yet another operating mode, the reactor can be filled with the terephthalic acid solution so as to provide no reactor vapor space. That is, the reactor can be operated as a hydraulically full system with dissolved hydrogen being fed to the reactor by flow control. In such an instance, the solution hydrogen concentration can be modulated by adjusting the hydrogen flow rate to the reactor. If desired, a pseudo-hydrogen partial pressure value can be calculated from the solution hydrogen concentration which, in turn, can be correlated with the hydrogen flow rate to the reactor.

In the operating mode where process control is effected by adjusting the hydrogen partial pressure, the hydrogen partial pressure in the reactor preferably is in the range of about 10 psi to about 200 psi, or higher, depending upon the service pressure rating of the reactor, the degree of contamination of the impure terephthalic acid, the activity and age of the particular catalyst employed, and like processing considerations.

In the operating mode where process control is effected by adjusting directly the hydrogen concentration in the feed solution, the latter usually is less than saturated with respect to hydrogen and the reactor itself is hydraulically full. Thus, an adjustment of the hydrogen flow rate to the reactor will result in the desired control of hydrogen concentration in the solution.

In general, the amount of hydrogen supplied to the purification reactor under reaction conditions is, of course, sufficient to effect the desired hydrogenation.

As described in the aforesaid U.S. Pat. Nos. 3,584,039; 3,726,915; and 4,405,809, catalysts that are suitable for use in the aforesaid purification step are insoluble under the conditions employed therein and comprise at least one supported or unsupported Group VIII noble metal, whose class includes palladium, rhodium, ruthenium, osmium, iridium, and platinum. Preferably, the noble metal is at least one of palladium and rhodium.

Preferably, the catalyst comprises a support. Preferred support materials include carbon and charcoal. Typically, the catalyst carrier is active carbon, usually that derived from coconut charcoal in the form of granules having a surface area of at least about 600 $m^2/g$ ($N_2$; BET Method), preferably about 800 $m^2/g$ to about 1,500 $m^2/g$. However, other porous carbonaceous supports or substrates can be used as long as the surface area requirements can be met. In addition to coconut charcoal, activated carbon derived from other plant or from animal sources can be utilized.

The noble metal component is present on the carrier at a concentration level in the range of about 0.01 weight percent to about 2 weight percent, based on the total weight of the catalyst, i.e., metal plus active carbon carrier, and calculated as the elemental noble metal. Preferably, the catalyst metal loading is about 0.5 weight percent.

A typical catalyst of palladium on a support comprises from about 0.01 to about 2 weight percent of palladium, based on the total weight of the catalyst and calculated as elemental metal. The support or carrier for the palladium is porous and inert, and preferably is active carbon having a surface area of about 600 $m^2/g$ to about 1,500 $m^2/g$. Suitable supports for Pd/C hydrogenation catalysts are well-known and are described, inter alia, in U.S. Pat. No. 3,584,039 to Meyer.

A suitable palladium-on-carbon catalyst can be obtained, for example, from Engelhard Corporation, Newark, N.J., under the designation "Palladium on Activated Carbon Granules (Carbon Code CG-5)." Similarly, suitable rhodium-on-carbon catalysts can be obtained from Engelhard Corporation, under the designations "Rhodium on Activated Carbon Granules (Carbon Code CG-5)" and "Rhodium on Activated Carbon Granules (Carbon Code CG-21)." Both of these catalysts have a BET; $N_2$ surface area of about 1,000 $m^2/g$ and have a particle size of 4×8 mesh, U.S. Sieve Series. Other suitable rhodium-on-carbon catalysts of similar size and surface area are available from Johnson Matthey Inc., Seabrook, N.H., under the designation "11766 Rhodium, 1% on Steam Activated Carbon Granules, Anhydrous."

The space velocity reported as weight of crude terephthalic acid solution per weight of catalyst per hour in the purification step is from about 5 hours$^{-1}$ to about 25 hours$^{-1}$, preferably from about 10 hours$^{-1}$ to about 15 hours$^{-1}$. The residence time of the solution in the catalyst bed varies, depending upon the activity of the catalysts present.

We have discovered that one of two major sources of fluorescence in purified terephthalic acid produced, using the aforesaid oxidation and purification steps and under the aforesaid conditions employed therein, are impurities which fluoresce at wavelengths of greater than 370, preferably 390–400, nanometers upon excitation by light at wavelengths of 260-320 nanometers and which are produced as by-products under the conditions described hereinabove generally employed in the aforesaid liquid-phase oxidation. These impurities are unreactive and insoluble in the solvents employed in the aforesaid oxidation and purification steps as to substantially remain in the terephthalic acid despite the purification processes to which they are subjected. These impurities can be separated from crude and purified terephthalic acid in the laboratory by reversed phase-liquid chromatography and can be detected fluorimetrically.

We have also discovered that the second of the two major sources in purified terephthalic acid produced using the aforesaid oxidation and purification steps and under the aforesaid conditions employed therein, of fluorescence at wavelengths of greater than 370, preferably 390-400, nanometers produced by excitation wavelengths between 260-320 nanometers is produced from other impurities therein which are also formed as by-products in the aforesaid liquid-phase oxidation of p-xylene, but which do not themselves fluoresce at wavelengths of greater than 370, preferably 390-400, nanometers under the aforesaid excitation conditions. However, upon chemical reduction during the aforesaid purification of the crude terephthalic acid product to form purified terephthalic acid, such impurities are converted to their reduced forms which do fluoresce at wavelengths of greater than 370, preferably 390-400, nanometers upon excitation by wavelengths of 260-320 nanometers.

Using a gradient high performance liquid chromatographic separation and a fluorimetric detection of the separated components, we have separated and determined either the specific identity, or at least the source, of the impurities that are produced in either the aforesaid oxidation step or the purification step under the aforesaid oxidation and purification conditions, respectively, employed therein and that account for substantially all of the fluorescence at wavelengths of greater than 370, preferably 390-400, nanometers produced by excitation wavelengths of 260-320 nanometers of crude terephthalic acid and purified terephthalic acid. Such impurities and their contributions to the fluorescence of both crude and purified terephthalic acid at wavelengths of greater than 370, preferably 390-400, nanometers produced by excitation wavelengths of 260-320 nanometers are presented in Table 1 hereinbelow.

TABLE 1

| Impurity | Contribution to the Fluorescence of | |
|---|---|---|
| | Crude Terephthalic Acid | Purified Terephthalic Acid |
| 4-carboxy-p-terphenyl | 1-7% | 1-7% |
| 4,4'-dicarboxybiphenyl | 1-7% | 1-7% |
| trans-4,4'-dicarboxy-stilbene | 50-80% | 0% |
| 4,4"-dicarboxy-p-terphenyl and 3-4"-dicarboxy-p-terphenyl | 20-50% | 20-50% |
| impurities formed in the purification step | 0% | 50-80% |

As the results presented in Table 1 illustrate, trans-4,4'-dicarboxystilbene, which accounts for at least 50 percent of the total fluorescence of crude terephthalic acid, is essentially completely removed from purified terephthalic acid as a result of the purification step. By contrast, 4,4'-dicarboxybiphenyl, 4-carboxy-p-terphenyl, 4,4"-dicarboxy-p-terphenyl, and 3,4"-dicarboxy-p-terphenyl are so insoluble and resistant to the purification step as to substantially remain in the purified terephthalic acid despite the purification process. Moreover, other unidentified fluorescent impurities which are not present in the crude terephthalic acid are formed in the purification process and account for at least 50 percent of the total fluorescence of purified terephthalic acid.

In view of the facts that an impurity representing a major source of fluorescence in crude terephthalic acid is quantitatively removed in the purification step and that other impurities representing a major source of fluorescence in purified terephthalic acid are not present in crude terephthalic acid but are produced in the purification step while still other fluorescent impurities in crude terephthalic acid are essentially unaffected by the purification step, it was highly surprising to find that changes in the concentration of one impurity, 4-carboxy-p-terphenyl, which is present in both crude and purified terephthalic acid correspond in a very predictable manner with changes in the concentrations of both (a) the other aforesaid impurities that are present in both crude and terephthalic acid and (b) the other aforesaid impurities that are formed in the purification step and are present in only purified terephthalic acid. The correspondence between variations of the concentration of 4-carboxy-p-terphenyl and variations of the concentrations of each of such other fluorescent impurities are presented in Table 2 hereinbelow.

TABLE 2

| Impurity | Correlation Between Variations of Concentration of 4-carboxy-p-terphenyl and Variations of Concentration of other Fluorescent Impurities in Purified Terephthalic Acid |
|---|---|
| A | 75.6 |
| B | 41.0 |
| 4,4"dicarboxy-p-terphenyl and 3,4"-dicarboxy-p-terphenyl combined | 87.7 |

The correlations shown in Table 2 are reported as the square of the correlation coefficient determined by linear regression analysis. In Table 2, A and B represent unidentified fluorescent materials which are produced during purification of crude terephthalic acid and together the fluorescence of A and B accounts for at least 90 percent of the fluorescence in purified terephthalic acid at wavelengths of greater than 370, preferably 390-400, nanometers produced by excitation wavelengths of 260-320 nanometers and resulting from fluorescent impurities produced during the aforesaid purification.

From the data in Tables 1 and 2, it is apparent that the concentrations of the other major fluorescent impurities in purified terephthalic acid and listed in Table 2 vary in a very predictable manner with changes in the concentration of 4-carboxy-p-terphenyl in or purified terephthalic acid. Thus, and as is confirmed by the data in Table 3, the fluorescence of purified terephthalic acid at wavelengths of greater than 370, preferably 390-400, nanometers produced by excitation wavelengths of 260-320 nanometers responds in a very predictable manner to the concentration of 4-carboxy-p-terphenyl in crude terephthalic acid.

We have discovered that the fluorescence of purified terephthalic acid is also a function of the optical density of the crude terephthalic acid from which it is made. Therefore, in order to eliminate or at least minimize the effect of variations of such optical density, the data presented in Table 3 are grouped into separate Categories A–F, with the various crude terephthalic acid products in each particular category having essentially the same optical densities, and the concentrations of 4-carboxy-p-terphenyl in the crude terephthalic acid products in that category are compared only with the fluorescence of purified terephthalic acid products in the same category. For the present purposes, the optical density of crude terephthalic acid is measured as the absorbence of light at 340 nanometers in a basic solution such as sodium hydroxide or ammonium hydroxide.

For each category illustrated in Table 3, the concentrations of 4-carboxy-p-terphenyl in crude terephthalic acid are plotted against the fluorescence of the resulting purified terephthalic acid in FIG. 1. The plots in FIG. 1 illustrate that, although the variation of the aforesaid fluorescence of purified terephthalic acid with the aforesaid concentration of 4-carboxy-p-terphenyl in the crude terephthalic acid from which it is made depends on the specific optical density of the crude terephthalic acid, for a given such optical density—for example, when such optical density is maintained at a constant level—the variation of the fluorescence of purified terephthalic acid with the concentration of 4-carboxy-p-terphenyl in crude terephthalic acid can be determined from plots like those illustrated in FIG. 1. In Table 3, the concentration of 4-carboxy-p-terphenyl in crude terephthalic acid is reported as parts per million by weight; the fluorescence of purified terephthalic acid is reported as the measured fluorometric peak height relative to that of a standard sample of purified terephthalic acid, and the optical density of crude terephthalic acid was measured using 2 samples of 3.25 grams of crude terephthalic acid in 50 milliliters of an aqueous solution of 4 molar ammonium hydroxide.

In addition or in the alternative—for example, when the optical density of the crude terephthalic acid is not maintained at a constant level—the optical density is determined by measurement, and the fluorescence of purified terephthalic acid can be calculated from the concentration of 4-carboxy-p-terphenyl and from the measured optical density as follows:

Fluorescence reported as relative peak height = −0.65 + 1.46 (concentration of 4-carboxy-p-terphenyl in crude terephthalic acid in parts per million by weight) + 0.73 (optical density of crude terephthalic acid at 340 nanometers).

This equation, which was determined from linear regression results for 60 samples of each of crude terephthalic acid products and of the purified terephthalic acid products made from them indicates that either a change of 0.1 part per million in the concentration of 4-carboxy-p-terphenyl in the crude terephthalic acid or a change of 0.2 unit in the optical density of the crude terephthalic acid results in about a 0.15 unit change in the fluorescence of purified terephthalic acid produced from it.

The essential feature of the method of this invention is the separation of 4-carboxy-p-terphenyl from a sample of the crude terephthalic acid produced using the oxidation method and conditions described hereinabove.

TABLE 3

| Category | Concentration of 4-Carboxy-p-terphenyl in Crude Terephthalic Acid | Optical Density of Crude Terephthalic Acid | Fluorescence of Purified Terephthalic Acid |
|---|---|---|---|
| A | 0.33 | 0.908 | 0.56 |
|   | 0.32 | 0.909 | 0.51 |
| B | 0.37 | 1.110 | 0.91 |
|   | 0.28 | 1.104 | 0.58 |
| C | 0.37 | 1.132 | 0.89 |
|   | 0.29 | 1.129 | 0.49 |
| D | 0.51 | 1.198 | 0.90 |
|   | 0.38 | 1.189 | 0.84 |
|   | 0.21 | 1.182 | 0.40 |
| E | 0.42 | 1.225 | 0.86 |
|   | 0.37 | 1.233 | 0.84 |
|   | 0.27 | 1.226 | 0.58 |
|   | 0.24 | 1.232 | 0.40 |
| F | 0.34 | 1.339 | 0.84 |
|   | 0.28 | 1.345 | 0.85 |
|   | 0.22 | 1.347 | 0.60 |
|   | 0.22 | 1.348 | 0.56 |

In the method of this invention, this separation is effected by an isocratic, high performance liquid chromatographic analysis of a sample of the crude terephthalic acid produced in the aforesaid oxidation before the aforesaid purification. The isocratic high performance liquid chromatographic separation can be effected using any conventional reversed-phase, nonpolar stationary phase. Particularly suitable reversed-phase stationary phases include octadecylsilane, octylsilane, or phenylsilane on a particulate silica gel support having a particle size in the range of 3 to 10 microns, preferably 5 microns. Columns prepacked with such stationary phases are commercially available.

It is essential that the mobile phase employed in the isocratic high performance liquid chromatographic separation of the method of this invention must contain: (1) from about 0.5 to about 10 percent by volume of at least one of acetic acid, formic acid, or an inorganic buffer such as a phosphate, (2) from about 20 to about 90 percent by volume of at least one of acetonitrile, tetrahydrofuran, methanol, ethanol, or isopropanol, and (3) from about 20 to about 80 volume percent of water. In addition, the mobile phase must have a pH in the range of from about 2 to about 5. A particularly suitable mobile phase is a solution containing about 5 volume percent of acetic acid and about 67.5 volume percent of acetonitrile and 27.5 volume percent of water and having a pH of 2.25.

Suitable flow rates of the mobile phase through the high performance liquid chromatography column are in the range of from about 0.5 to about 4 milliliters per minute, and a particularly suitable such flow rate is 2 milliliters per minute. The pressure employed in the chromatographic separation suitably needs only to be high enough to overcome the back pressure of the column and typically is in the range of from about 500 to about 2000 psi.

The resulting chromatogram has only 2 peaks, a sharp second peak corresponding to 4-carboxy-p-terphenyl which elutes from the column after a broad first peak corresponding to all of the remaining fluorescent impurities in the crude terephthalic acid.

Any conventional flow-through fluorimetric detector, such as a Perkin Elmer Model LS-4 or a Kratos FS 970 fluorimetric detector, can be employed to monitor the excitation radiation of wavelengths of 260–320 nanometers and resulting fluorescent radiation of wavelengths of greater than 370, preferably 390–400, nanometers can be employed.

An external standard of 4-carboxy-p-terphenyl is employed for the calculation of the concentrations of 4-carboxy-p-terphenyl in the crude terephthalic acid products from the measured peak areas or peak heights therefor.

More particularly, the following conditions were employed in the chromatographic separation employed to obtain the concentrations of 4-carboxy-p-terphenyl shown in Table 3 hereinabove: A column having a 5-centimeter length and a 4.6-millimeter inside diameter packed with octadecylsilane on particulate silica having a particle size of 3 microns, a mobile phase of 67.5 volume percent of acetonitrile, 27.5 volume percent of water and 5 volume percent of acetic acid flowing at 2.0 milliliters per minute and 1400 psi.

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

Having described the invention, what is claimed is:

1. In a method for producing purified terephthalic acid comprising: oxidizing in the liquid-phase p-xylene with an oxygen-containing gas in a solvent at an elevated temperature and pressure and in the presence of an oxidation catalyst comprising cobalt, manganese, and bromine components to form crude terephthalic acid and impurities comprising 4-carboxy-p-terphenyl; reducing in the liquid phase at least a portion of the impurities in the resulting crude terephthalic acid in an aqueous solution at an elevated temperature and pressure and in the presence of hydrogen and at least one insoluble Group VIII noble metal-containing catalyst; separating the solid noble metal-containing catalyst from the aqueous solution; and crystallizing and separating the purified terephthalic acid from the aqueous solution while maintaining the temperature in the range of 50°–150° C., and monitoring the purity of the purified terephthalic acid; the improvement wherein the monitoring comprises monitoring the fluorescence at wavelengths of greater than 370 nanometers produced by excitation wavelengths of 260–320 nanometers of 4-carboxy-p-terphenyl in the crude terephthalic acid, and variations therein, by separating 4-carboxy-p-terphenyl from a sample of the crude terephthalic acid having a predetermined optical density at 340 nanometer wavelengths, by isocratic, high performance liquid chromatography using a reversed-phase nonpolar stationary phase and a mobile phase comprising: a solution of (1) from about 0.5 to about 10 volume percent of at least one of acetic acid, formic acid, or an inorganic buffer: (2) from about 20 to about 90 volume percent of at least one of acetonitrile, tetrahydrofuran, methanol, ethanol, or isopropanol, and (3) from about 20 to about 80 volume percent of water and has a pH of from about 2 to about 5 and measuring the fluorescence of the separated 4-carboxy-p-terphenyl at wavelengths of greater than 370 nanometers produced by excitation wavelengths of 260–320 nanometers whereby fluorescence, and variations therein, of the 4-carboxy-p-terphenyl provide an indication of the fluorescence of the purified terephthalic acid.

2. The method of claim 1 wherein the solvent in the oxidation step is a $C_2$–$C_6$ monocarboxylic acid, water, or a mixture thereof.

3. The method of claim 2 wherein the solvent in the oxidation step is a mixture of acetic acid and water containing from 1 to 20 weight percent of water in the reactor.

4. The method of claim 1 wherein the catalyst in the purification step comprises at least one Group VIII noble metal-containing component on a carbon support.

5. The method of claim 4 wherein the catalyst in the purification step comprises at least a palladium-containing component on a carbon support.

6. The method of claim 1 wherein the mobile phase comprises water, acetic acid, and acetonitrile.

7. The method of claim 6 wherein the mobile phase comprises from about 25 to about 40 weight percent of water, from about 2 to about 7 weight percent of acetic acid and from about 60 to about 75 weight percent of acetonitrile.

8. The method of claim 7 wherein the mobile phase consists essentially of water, acetic acid, and acetonitrile.

9. The method of claim 1 wherein the mobile phase has a pH of 2–3.

* * * * *